(12) United States Patent
Schein et al.

(10) Patent No.: US 8,361,091 B2
(45) Date of Patent: Jan. 29, 2013

(54) CANNULAS, CANNULA MOUNT ASSEMBLIES, AND CLAMPING METHODS USING SUCH CANNULAS AND CANNULA MOUNT ASSEMBLIES

(75) Inventors: Douglas A. Schein, Chicago, IL (US); David W. Wright, Littleton, CO (US); Raymond Sirianne, Evergreen, CO (US); Philip D. Palermo, Marietta, GA (US); Russell J. Kroll, Atlanta, GA (US); John M. Brassil, Northbrook, IL (US)

(73) Assignee: Organ Recovery Systems, Inc., Des Plaines, IL (US)

( * ) Notice: Subject to any disclaimer, the term of this patent is extended or adjusted under 35 U.S.C. 154(b) by 2042 days.

(21) Appl. No.: 10/646,801

(22) Filed: Aug. 25, 2003

(65) Prior Publication Data

US 2004/0111104 A1 Jun. 10, 2004

Related U.S. Application Data

(60) Provisional application No. 60/460,875, filed on Apr. 8, 2003, provisional application No. 60/405,321, filed on Aug. 23, 2002.

(51) Int. Cl.
*A61B 17/08* (2006.01)
(52) U.S. Cl. .......................... 606/151; 606/153
(58) Field of Classification Search .................. 606/153; 435/284.1; 128/DIG. 26; 604/8
See application file for complete search history.

(56) References Cited

U.S. PATENT DOCUMENTS

| | | | |
|---|---|---|---|
| 3,406,531 A | 10/1968 | Swenson et al. | |
| 3,538,915 A * | 11/1970 | Frampton et. al. | ............ 604/272 |
| 3,545,221 A | 12/1970 | Swenson et al. | |
| 3,607,646 A | 9/1971 | de Roissart | |
| 3,654,085 A | 4/1972 | Norr et al. | |
| 3,660,241 A | 5/1972 | Michielsen | |
| 3,777,507 A | 12/1973 | Burton et al. | |
| 3,810,367 A | 5/1974 | Peterson | |
| 3,843,455 A | 10/1974 | Bier | |

(Continued)

FOREIGN PATENT DOCUMENTS

| DE | 38 08 942 | 9/1989 |
|---|---|---|
| DE | 43 24 637 A1 | 3/1995 |

(Continued)

OTHER PUBLICATIONS

U.S. Appl. No. 60/459,986, filed Apr. 4, 2003, David W. Wright et al.

(Continued)

*Primary Examiner* — Gary Jackson
*Assistant Examiner* — Diane Yabut
(74) *Attorney, Agent, or Firm* — Oliff & Berridge, PLC

(57) ABSTRACT

A cannula connects an organ with a perfusion system that monitors, treats, sustains and/or restores the viability of the organ and/or that transports and/or stores the organ. At least part of a cannula may be made of a soft elastomer to help avoid damage to the organ. In embodiments, the cannula includes a top portion, a bottom portion, a sealing ring and two compression straps. In embodiments, the cannula includes a top portion and a flexible bottom portion that may be attached to the top portion. In embodiments, part of the cannula is inserted directly into an artery and a suture is used to tie the artery in place. Also, the cannula may include an attachment feature that can be used to connect the cannula to an organ platform or chair. Various features of the cannula may allow a visual check for and venting of air bubbles in the cannula.

48 Claims, 10 Drawing Sheets

U.S. PATENT DOCUMENTS

| | | | |
|---|---|---|---|
| 3,877,843 A | 4/1975 | Fischel | |
| 3,881,990 A | 5/1975 | Burton et al. | |
| 3,914,954 A | 10/1975 | Doerig | |
| 3,935,065 A | 1/1976 | Doerig | |
| 3,995,444 A | 12/1976 | Clark et al. | |
| 4,006,744 A | 2/1977 | Steer | 128/214 R |
| 4,186,565 A | 2/1980 | Toledo-Pereyra | |
| 4,242,883 A | 1/1981 | Toledo-Pereyra | |
| 4,462,215 A | 7/1984 | Kuraoka et al. | |
| 4,471,629 A | 9/1984 | Toledo-Pereyra | |
| 4,473,637 A | 9/1984 | Guibert | |
| 4,474,016 A | 10/1984 | Winchell | |
| 4,494,385 A | 1/1985 | Kuraoka et al. | |
| 4,502,295 A | 3/1985 | Toledo-Pereyra | |
| 4,723,974 A | 2/1988 | Ammerman | |
| 4,745,759 A | 5/1988 | Bauer et al. | |
| 4,766,740 A | 8/1988 | Bradley et al. | |
| 4,800,879 A * | 1/1989 | Golyakhovsky et al. | 606/158 |
| 4,837,390 A | 6/1989 | Reneau | |
| 4,951,482 A | 8/1990 | Gilbert | |
| 4,958,506 A | 9/1990 | Guilhem et al. | |
| 5,004,457 A | 4/1991 | Wyatt et al. | 604/158 |
| 5,141,847 A | 8/1992 | Sugimachi et al. | |
| 5,157,930 A | 10/1992 | McGhee et al. | |
| 5,217,860 A | 6/1993 | Fahy et al. | |
| 5,285,657 A | 2/1994 | Bacchi et al. | |
| 5,326,706 A | 7/1994 | Yland et al. | |
| 5,356,771 A | 10/1994 | O'Dell | |
| 5,362,622 A | 11/1994 | O'Dell et al. | |
| 5,383,854 A | 1/1995 | Safar et al. | |
| 5,385,821 A | 1/1995 | O'Dell et al. | |
| 5,434,045 A | 7/1995 | Jost | |
| 5,472,876 A | 12/1995 | Fahy | |
| 5,586,438 A | 12/1996 | Fahy | |
| 5,681,740 A | 10/1997 | Messier et al. | |
| 5,723,282 A | 3/1998 | Fahy et al. | |
| 5,728,115 A * | 3/1998 | Westcott et al. | 606/151 |
| 5,814,016 A * | 9/1998 | Valley et al. | 604/96.01 |
| 5,821,045 A | 10/1998 | Fahy et al. | |
| 5,856,081 A | 1/1999 | Fahy | |
| 5,965,433 A | 10/1999 | Gardetto et al. | |
| 6,046,046 A | 4/2000 | Hassanein | |
| 6,355,010 B1 * | 3/2002 | Barbut | 604/8 |
| 6,726,651 B1 * | 4/2004 | Robinson et al. | 604/101.01 |

FOREIGN PATENT DOCUMENTS

| | | |
|---|---|---|
| EP | 0 096 997 | 12/1983 |
| EP | 0 376 763 A2 | 7/1990 |
| GB | 1442356 A | 7/1976 |
| JP | 2-258701 | 10/1990 |
| SU | 760972 | 9/1980 |
| WO | WO 91/03934 | 4/1991 |
| WO | WO 91/14364 | 10/1991 |
| WO | WO 93/00808 | 1/1993 |
| WO | WO 96/05727 | 2/1996 |
| WO | WO 96/13288 | 5/1996 |
| WO | WO 96/29865 | 10/1996 |
| WO | WO 96/30111 | 10/1996 |
| WO | WO 97/45527 | 12/1997 |
| WO | WO 99/15011 | 4/1999 |
| WO | WO 00/18226 | 4/2000 |
| WO | WO 02/26034 A | 4/2002 |

OTHER PUBLICATIONS

U.S. Appl. No. 60/459,981, filed Apr. 4, 2003, David W. Wright et al.
"Organ Preservation", J.H. Southard, Ph.D. and F.O. Belzer, M.D., *Principles of Organ Transplantation*, Chapter 10, pp. 194-215, 1989.
"Organko Servierungsmachine Okm 82", Von Dietmer Scholz et al., East German Article, 1983.w/translation.
"Preservation of Cerebral Function During Circulatory Arrest and Resuscitation: Hypothermic Protective Considerations", Robert J. White, *Resuscitation*, vol. 1, pp. 107-115, 1972.
"Storage and Transport of Heart and Heart-Lung Donor Organs With Inflatable Cushions and Eutectoid Cooling", D.R. Wheeldon et al., *The Journal of Heart Transplantation*, vol. 7, pp. 265-268, 1988.
"MOX®-100 Renal Preservation System", Waters Instruments Medical Group, pp. 2-7, 1982.
"Organ Perfusion Systems: An Evaluation Criteria", Fereydoon Sadri, Ph.D., *T.O.P.S. Medical Corporation*, pp. 1-8, 1987.
Gauke Kootstra et al, "A New Device Towards Intermediate Term Kidney Preservation—An Experimental Study," 1980, pp. 86-89.

* cited by examiner

CANNULAS, CANNULA MOUNT ASSEMBLIES, AND CLAMPING METHODS USING SUCH CANNULAS AND CANNULA MOUNT ASSEMBLIES

BACKGROUND OF THE INVENTION

This nonprovisional application claims the benefit of U.S. Provisional Application No. 60/460,875, filed Apr. 8, 2003 and Provisional Application No. 60/405,321, filed Aug. 23, 2002.

The invention relates to cannulas and clamping methods. More specifically, the invention relates to cannulas, cannula mount assemblies and clamping methods for perfusing one or more organs to monitor, treat, sustain and/or restore the viability of the organ(s) and/or for transporting and/or storing the organ(s).

Various devices have been developed that couple the anatomy of an organ being perfused to a machine or other equipment. Such devices are typically referred to as perfusion clamps or simply cannulas. Although the term cannula in general use has other meanings, the term cannula is used generically throughout the specification to refer to a clamp or other device that provides a connection through which a fluid flow may be established.

Currently, perfusionists select between two types of cannulas, depending on whether an aortic patch is available. A first type of cannula, as described in U.S. Pat. No. 5,728,115 to Westcott et al., which is hereby incorporated by reference, is shown in FIGS. 1-3. A clamping device (cannula) 10 is used to couple the perfusion cannula to the renal aorta 34. The clamp 10 includes two longitudinal members 12 and 14 which pivot about a pin 16. The proximal end of the member 12 includes an integral handle 18, while the proximal end of the member 14 includes an integral handle 20. The distal end of the member 12 includes an integral clamp head 24, while the distal end of the member 14 includes an integral clamp head 26. Clamp head 26 includes a nipple 28 attached thereto. Movement of the handles 18 and 20 toward one another forces the members 12 and 14 to pivot about the pin 16, thereby forcing the clamp heads 24 and 26 of the members 12 and 14 away from one another. A spring 22 is positioned between the handles 18 and 20 in order to bias the handles apart. This, in turn, tends to force the clamp heads 24 and 26 together. Therefore, the clamp heads 24 and 26 of the distal ends of the members 12 and 14 are engaged in clamping relationship unless an external compressive force is applied to the handles 18 and 20.

The distal end of the member 12 comprises an elongated, hollow, annular clamp head 24. A lumen 32 extends through the nipple 28.

In use, the clamp 10 is attached to the renal aorta 34 of a donor organ such as a kidney 36 by opening the clamp 10, passing the distal end 38 of the renal aorta 34 through the annular clamp head 24, holding the distal end 38 of the renal aorta 34 over the annular clamp head 24, and releasing pressure on the handles of the clamp 10 in order to allow the clamp head 26 to engage the distal end 38 of the renal aorta 34 against the annular clamp head 24. A catheter 40 may then be attached to the nipple 28 in order to provide perfusion of liquid through the lumen 32 and into the renal aorta 34.

A second type of cannula 50, used when no aortic patch is available, is shown in FIG. 4. No aortic patch may be available due to anatomical constraints or a living donor recovery. An infuse line (not shown) is connected to a top tube portion 52 of the cannula 50. A lower tube portion 54 of the cannula is inserted into the renal artery. The lower tube portion 54 may be sutured into place.

SUMMARY OF THE INVENTION

The present invention focuses on avoiding damage to an organ during perfusion while connecting the organ to a machine or system for monitoring, treating, sustaining and/or restoring the viability of the organ and preserving the organ for storage and/or transport. The invention is directed to apparatus and methods for connecting an organ to be perfused with a perfusion machine or system that monitors, treats, sustains and/or restores the viability of the organ and/or that transports and/or stores the organ. In particular, apparatus and methods according to the invention are suitable for use with the perfusion systems and methods described in U.S. Pat. No. 6,209,343, which is hereby incorporated by reference in its entirety. Thus, apparatus and methods according to the invention are suitable for use with organ perfusion at normothermic temperatures and organ perfusion at hypothermic temperatures. Apparatus and methods according to the invention are suitable for use with an organ cassette, such as that disclosed in the '525 application, and/or with a mother unit, and/or with a portable transport apparatus, such as, for example, a cooler or a portable container such as that disclosed in co-pending U.S. application Ser. No. 09/161,919, filed Sep. 29, 1998, which is hereby incorporated by reference in its entirety. The apparatus and methods according to the invention are also suitable for use with the organ cassette systems and methods described in copending U.S. Provisional Applications Nos. 60/459,986 and 60/459,981, filed Apr. 4, 2003, which are hereby incorporated by reference in their entirety.

Various exemplary embodiments of apparatus and methods according to the invention are atraumatic to the aortic patch or general tissue that is to be connected. In various exemplary embodiments, soft medical grade elastomers are utilized to contact the delicate inner wall of the patch or tissue. In various exemplary embodiments, the sealing force is spread out over a large surface area, helping to reduce the force on a specific section of the patch or tissue.

Various exemplary embodiments of apparatus and methods according to the invention seal against aortic patches or other tissue with a hard plaque build-up. In various exemplary embodiments, an elastomeric sealing ring is used that follows the contour of plaque build-up. In various exemplary embodiments, a relatively large sealing surface provides good contact.

Various exemplary embodiments of apparatus and methods according to the invention provide visual access to an air bubble trap. In various exemplary embodiments, at least a portion of the cannula is made of a translucent material to provide viewing into an upper portion of the cannula that traps air bubbles.

Various exemplary embodiments of apparatus and methods according to the invention provide a means to prime and/or vent air bubbles from the cannula, connecting tubes and/or the organ without disconnecting the cannula from the tissue. In various exemplary embodiments, a fitting allows the user to open a port to let air out.

Various exemplary embodiments of apparatus and methods according to the invention provide a means to handle organs with multiple arteries. In various exemplary embodiments, a relatively large sealing ring accommodates patches or tissues containing multiple arteries. In various exemplary embodiments, a fluid exit may be shaped to accommodate patches or tissues containing multiple arteries. In various exemplary embodiments, a fitting allows the user to network multiple cannulas that are each connected to patches or placed straight into an artery.

Various exemplary embodiments of apparatus and methods according to the invention allow an aortic patch or tissue to be positioned and fixed to the cannula prior to clamping. In various exemplary embodiments, the aortic patch or tissue may be located and fixed onto flanges prior to clamping, for example, with standard surgical clamps.

Various exemplary embodiments of apparatus and methods according to the invention allow an artery to be held at a fixed tension. In various exemplary embodiments, the cannula includes locating or positioning features that may be securely positioned, for example, onto an organ platform or chair, such as the chair described in the incorporated '525 application, to keep the artery from getting twisted and/or stressed.

Various exemplary embodiments of apparatus and methods according to the invention provide parallel sealing surfaces. In various exemplary embodiments, the sealing surfaces are not constrained by a hinge, allowing the surfaces to remain parallel during clamping.

Various exemplary embodiments of apparatus and methods according to the invention provide a secure connection to an infuse line. In various exemplary embodiments, a locking fitting ensures a secure, leak-proof connection to tubing of a perfusion machine or system.

Various exemplary embodiments of apparatus and methods according to the invention provide a cannula that is suitable for multiple size organs, i.e., one-size-fits-all. In various exemplary embodiments, a bottom portion of the cannula may be shaped, for example with standard scissors or knives, to accommodate various patch sizes and multiple arteries.

Various exemplary embodiments of apparatus and methods according to the invention allow the aortic patch or tissue to be in a natural position. In various exemplary embodiments, an inner clamp surface can be shaped cylindrically to allow the aortic patch or tissue to be fixed in its natural shape.

BRIEF DESCRIPTION OF THE DRAWINGS

These and other aspects and advantages of the invention will become apparent from the following detailed description of exemplary embodiments when taken in conjunction with the accompanying drawings, in which.

DETAILED DESCRIPTION OF EXEMPLARY EMBODIMENTS

Preservation of organs by machine perfusion has been accomplished at hypothermic temperatures with or without computer control with crystalloid perfusates and without oxygenation. See, for example, U.S. Pat. Nos. 5,149,321, 5,395,314, 5,584,804, 5,709,654 and 5,752,929 and U.S. patent application Ser. No. 08/484,601 to Klatz et al., which are hereby incorporated by reference.

Ideally organs would be procured in a manner which limits their warm ischemia time to essentially zero. Unfortunately, in reality, many organs, especially from non-beating heart donors, are procured after extended warm ischemia time periods (i.e. 45 minutes or more). The machine perfusion of these organs at low temperature has demonstrated significant improvement (Transpl Int 1996 Daemen). Numerous control circuits and pumping configurations have been utilized to achieve this objective and to machine perfuse organs in general. See, for example, U.S. Pat. Nos. 5,338,662 and 5,494, 822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thome et al.; U.S. Pat. Nos. 5,285,657 and 5,476,763 to Bacchi et al.; U.S. Pat. No. 5,157, 930 to McGhee et al.; and U.S. Pat. No. 5,141,847 to Sugimachi et al., which are hereby incorporated by reference.

The cannulas and clamping methods according to the invention may be used in conjunction with apparatus and methods described in U.S. Pat. Nos. 6,014,864, 6,183,019, 6,241,945 and 6,485,450 to Owen, which are hereby incorporated by reference. While these apparatus and methods are related to organ recovery and transplantation, the cannulas and clamping methods according to the invention may also be used in various other medical procedures and with various other medical equipment where clamping with fluid flow is desired. Thus, the cannulas and clamping methods according to the invention are not limited to the applications described below in conjunction with the exemplary embodiments.

Figure 1:
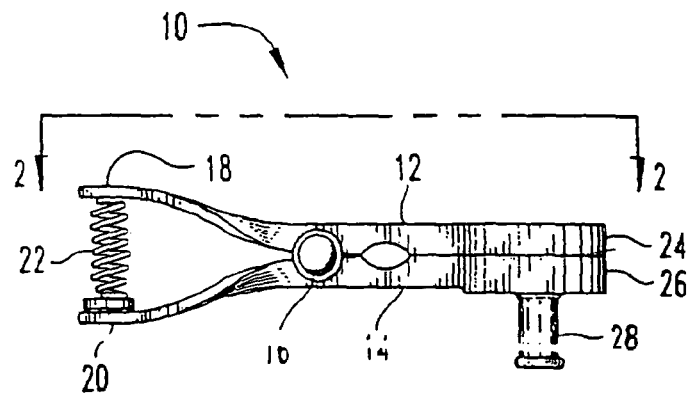
FIGS. 1-3 show a first type of a known perfusion clamp or cannula.
Figure 2:
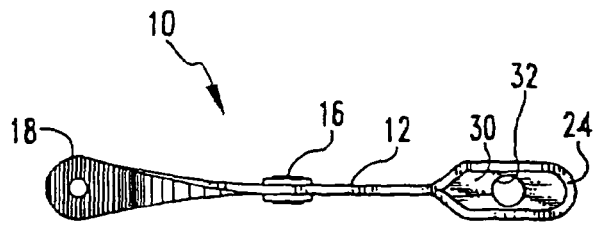
Figure 3:
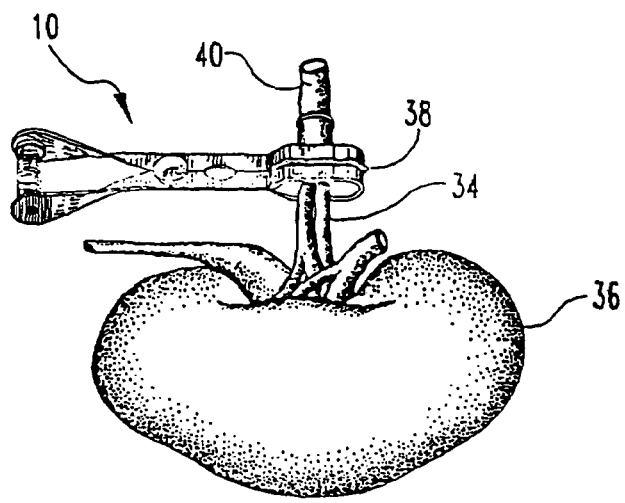
Figure 4:
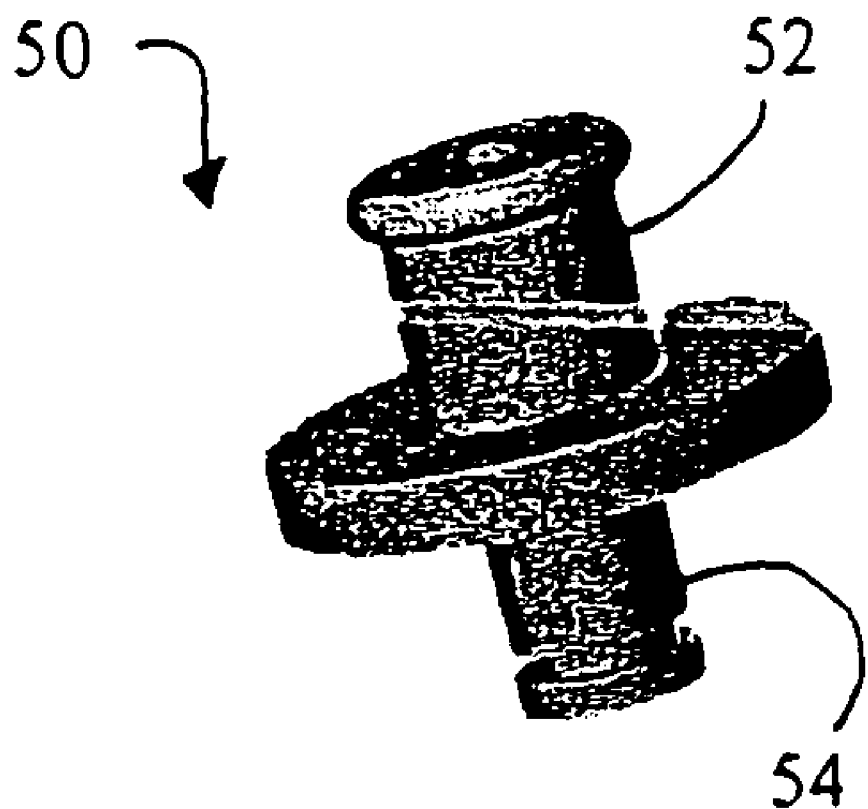
FIG. 4 shows a second type of a known perfusion clamp or cannula.
Figure 5:
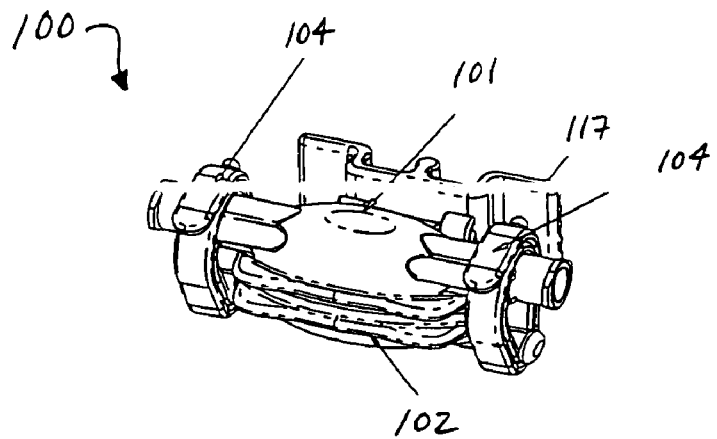
FIG. 5 is a perspective view of a first exemplary embodiment of a cannula and a cannula mount according to the invention.

FIG. 5 shows a perfusion clamping apparatus or cannula 100 according to a first exemplary embodiment of the invention. The cannula 100 is capable of connecting one or more arteries of an organ to a perfusion machine or system (not shown), for example, by connection to tubing of the perfusion machine or system. All medical fluid contact surfaces are preferably formed of or coated with materials compatible with the medical fluid used, preferably non-thrombogenic materials.

The medical fluid for perfusion may be any suitable medical fluid. For example, it may be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in tissue protection. Further, the medical fluid may also include blood or blood products.

Figure 6:
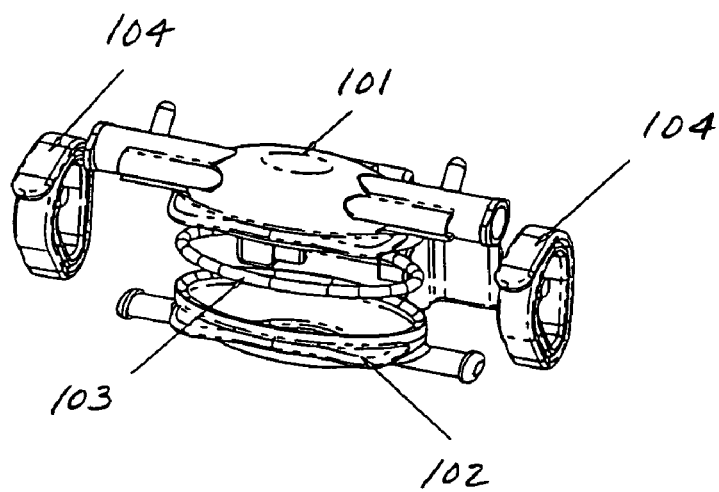
FIG. 6 is an exploded view of the first embodiment shown in FIG. 5.

The cannula 100 is shown in FIG. 5 in a closed or clamping condition and in FIG. 6 in an exploded condition. The cannula 100 comprises a top portion 101, a bottom portion 102, a sealing ring 103 and compression straps 104. Also, the cannula 100 may include a cannula mount in the from of a locating or positioning structure 117 that can be used to connect the cannula 100 to an organ platform or chair (not shown). While the relative terms "top" and "bottom" are used to refer to the various embodiments as shown in the Figs. throughout this application, it should be understood that the various parts may be otherwise oriented, and that the relative terms "top" and "bottom" are not limiting.

The top and bottom portions 101 and 102 seal to an aortic patch or other tissue by clamping the aortic patch or other tissue therebetween. The compression straps 104 are used to force the top portion 101 and the bottom portion 102 together and may be made of a resilient material, such as an elastomer. The sealing ring 103 may or may not be captured between the aortic patch or other tissue and the top portion 101 or the bottom portion 102, or two sealing rings 103 may be present and captured between each of the top and bottom portions 101, 102 and the aortic patch or other tissue. The sealing ring 103 may be included or not, and may be incorporated into either or both sealing surfaces of the top and bottom surfaces 101 and 102, described below.

The top portion 101 has a fitting 105 that is used to connect to a perfusion machine or other fluid source, for example, by tubing (not shown). The top portion 101, or a portion thereof, may be constructed of a clear or translucent material that allows a user to visually check for air bubbles. Any air that is present in the cannula will collect at an upper portion 106 of the top portion 101.

Various exemplary embodiments of the cannulas according to this invention provide a "lateral" fluid flow, i.e., a flow of fluid that is substantially perpendicular to the direction of fluid flow to and from the tissue to which the cannula is attached. For example, the one or more fittings of the cannula are oriented to have an axis of fluid flow that is substantially perpendicular to an axis of fluid flow into/out of the hole or lumen of the cannula. This "lateral" fluid flow arrangement allows the cannula to be connected to tubing of an organ transporter, for example, that is substantially in a single plane, for example, as described in the incorporated U.S. Provisional Applications Nos. 60/459,986 and 60/459,981). Further, multiple cannulas may be connected and even interconnected within substantially the same plane.

A second fitting 107 may be provided on the top portion 101 for priming and/or air bubble removal. The second fitting 107 comprises a port or valve for such purpose. The second fitting 107 may also be used to network multiple cannulas, for example, by connecting tubing in parallel, for example, by running a split infuse line to the first fitting of each cannula, or in series, for example, by connecting the first fitting of a cannula to the second fitting of another cannula. Standard luer geometry or other suitable structure may be used for fittings 105 and 107.

Figure 7:
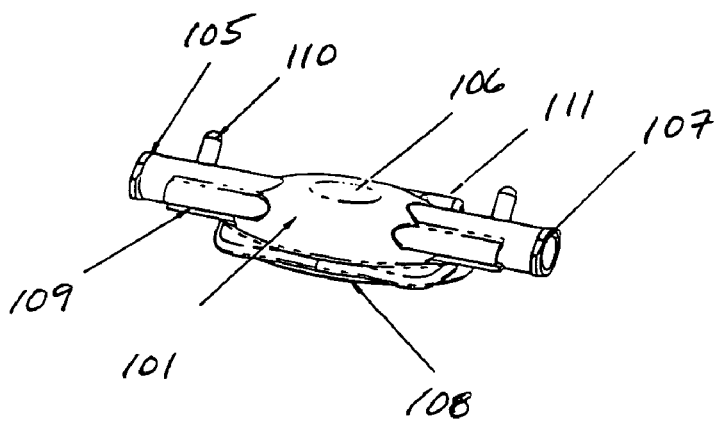
FIG. 7 is a perspective view of a top portion of the first embodiment shown in FIG. 5.

As shown in FIG. 7, the top portion 101 has a top sealing surface 108. The top sealing surface 108 may be made of a soft elastomer, such as, for example, SANTOPRENE® made by advanced Elastomer Systems. Any other suitable materials may be used as well, such as silicone or flexible polyvinylchloride (PVC) and the like. The top sealing surface 108 is shown in this embodiment as elliptical, although other suitable shapes, such as oval, circular and rectangular are also contemplated. The top sealing surface 108 may include ribs, ridges, cuts and/or protrusions that create a tortuous fluid path. The tortuous path serves to increase surface area by providing bends, turns and/or edges that increase the robustness of the seal and/or the likelihood of a sufficient seal.

The top portion 101 may include engagement members 109 that accept a free end of the compressions straps 104 and fixing members 110 that hold a portion of the compression straps 104 with the cannula 100 in a clamping condition. While the engagement members 109 are shown as slots in this embodiment, any suitable structure or technique, either known or hereafter developed, that provides attachment or retention of a free end of the straps 104 may be used. The top portion 101 may also have a pre-positioning structure 111, as discussed further below.

While the engagement members 109 and fixing members 110 are shown as part of the top portion 101, these members may be part of the bottom portion 102. In other words, such features of the cannula 100 may be reversed.

Figure 8:
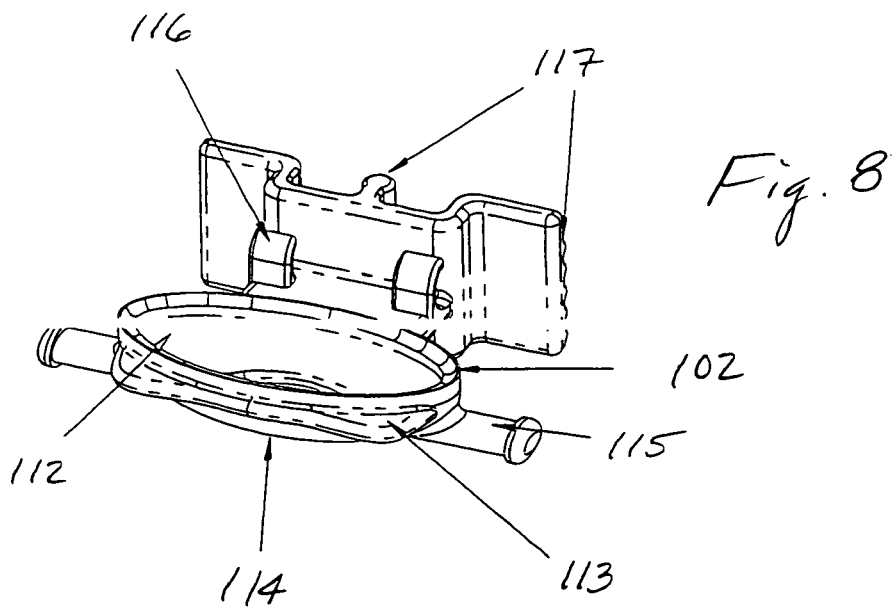
FIG. 8 is a perspective view of a bottom portion of the first embodiment shown in FIG. 5, shown with the cannula mount.

As shown in FIG. 8, the bottom portion 102 has a bottom sealing surface 112 that mates with the top sealing surface 108. The bottom sealing surface 112 may be made of a soft elastomer, as with the top sealing surface 108. The bottom sealing surface 112 may also have ribs, ridges, cuts and/or protrusions that create a tortuous fluid path.

The bottom portion 102 may include flanges or other protrusions 113 near the bottom sealing surface 112. The flanges 113 may be used to position the aortic patch or other tissue prior to assembly, for example, by clamping the aortic patch or other tissue to the flanges 113 with common surgical tools.

A hole 114 may be located in the bottom portion 102. The aortic patch or other tissue is positioned by feeding the patch through the hole 114 and laying and/or spreading the patch across the bottom sealing surface 112. The hole 114 may be designed to accept varying patch or other tissue sizes and/or patches or other tissues with multiple arteries.

The bottom portion 102 may include posts 115 that protrude outwardly. In use, the compression straps 104 can be wrapped around the posts 115. Other suitable structures, either known or hereafter developed, that are capable of pressing and holding the top and bottom portions 101 and 102 together may be used in place of the compression straps 104. For example, rigid clips or compliant springs may be used in place of the compression straps 104. Such clips or springs may be made of any suitable material, such as metal or plastic.

The bottom portion 102 may include complementary pre-positioning structure 116 that complements the pre-positioning structure 111 of the top portion 101. In the embodiment shown in FIGS. 7-8, the pre-positioning structure 111 is shown as a bar and the complementary pre-positioning structure 116 is shown as a pair of hooks or flanges. The hooks or flanges preferably engage the bar to allow the sealing surfaces 108 and 112 of the top and bottom portions 101 and 102 to remain parallel prior to closure and clamping. It should be understood that the structures 111 and 116 may be any suitable structures, either known or hereafter developed, that cooperate to provide pre-positioning of the top and bottom portions 101 and 102.

As shown in FIG. 8, the locating or positioning structure 117 may be connected to the bottom portion 102, although it may alternatively or additionally be connected to the top portion 101. The positioning structure 117 is designed to position the cannula 100 relative to the organ and/or the organ platform or chair. The positioning structure 117 may also be designed to position the artery relative to the cannula 100 and/or the organ. The positioning structure 117 helps to hold the artery at a fixed tension and helps to keep the artery from getting twisted or stressed by securely positioning the cannula 100 onto the organ platform or chair.

The configuration and/or features of the positioning structure 117 will vary depending on the configuration of the organ platform or chair. For example, a post near a middle of the positioning structure 117 may provide a snap-fit with a corresponding structure of the organ platform or chair. Further, horizontal ribs or a washboard structure may engage or mate with a corresponding structure of the organ platform or chair. Other fastening arrangements including, but not limited to, clips, clamps, snaps, hook and loop fasteners (e.g., VELCRO® fasteners) and multi-part systems are contemplated as well.

Figure 9:
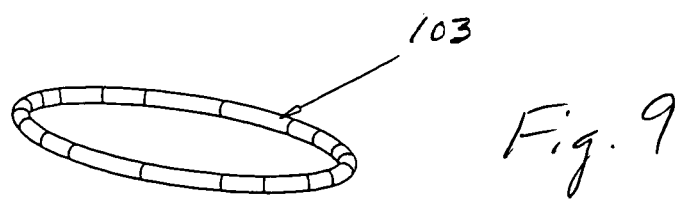
FIG. 9 is a perspective view of a sealing ring of the first embodiment shown in FIG. 5.

An exemplary sealing ring 103 is shown in detail in FIG. 9. The sealing ring 113 may be shaped corresponding to the shape of the top and/or bottom portions 101 and 102, particularly the top and bottom sealing surfaces 108 and 112. The sealing ring 103 may be constructed of a soft material, such as SANTOPRENE® made by advanced Elastomer Systems, silicone or flexible polyvinylchloride (PVC) and the like, which allows the sealing ring 103 to surround and follow the contour of plaque or calcium deposits on the aortic patch or other tissue. The sealing ring 103 may also have details that help to locate the top portion 101 relative to the bottom portion 102 prior to closure. For example, undercuts in the sealing ring 103 may be arranged to mate with corresponding ribs formed on the top and/or bottom portions 101 and 102. Alternatively, the sealing ring 103 may be made integral with the top and/or bottom portions 101 and 102.

Figure 10:
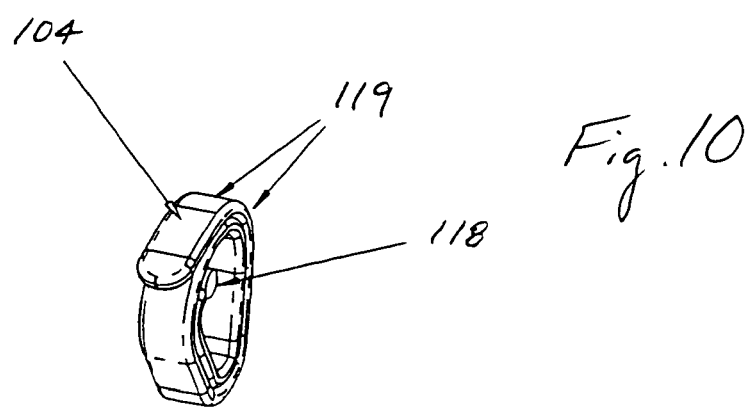
FIG. 10 is a perspective view of a compression strap of the first embodiment shown in FIG. 5.

An exemplary compression strap 104 is shown in detail in FIG. 10. A free end of the compression strap 104 preferably has a shaped end or flange 118 that is configured to be engaged by engagement members 109 of the top portion 101. The tension of the compression strap 104 may be varied, for example, by engaging one of a plurality of holes 119 to fixing members 110 of the top portion 101. A textured surface, such as ridges, may be located at an end of the compression strap 104 (opposite the flange 118) to increase a user's grip for tensioning the compression strap 104. As the compression straps 104 are tensioned in use, the top and bottom portions 101 and 102 of the cannula 100 are pulled together to create a seal.

Figure 11:
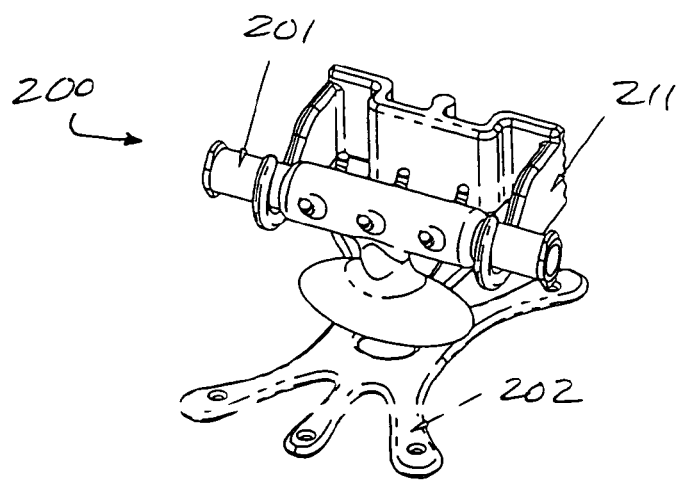
FIG. 11 is a perspective view of a second exemplary embodiment of a cannula and a cannula mount according to the invention.

FIG. 11 shows a perfusion clamping apparatus or cannula 200 according to a second exemplary embodiment of the invention. The cannula 200 is shown in FIG. 11 in an open condition. The cannula 200 comprises a top portion 201 and a bottom portion 202. Also, the cannula 200 may include a cannula mount or positioning structure 211 that can be used, for example, to connect the cannula 200 to an organ platform or chair (not shown).

In use, the aortic patch or other tissue associated with the organ is compressed between the top portion 201 and the bottom portion 202 to create a fluid seal to the patch or other tissue. A large surface area of the patch or other tissue is compressed, which allows a relatively low force to be used to achieve a suitable seal. The large sealing surface of this embodiment provides good contact to seal, for example, against aortic patches or other tissues with a hard plaque build-up.

Figure 12:
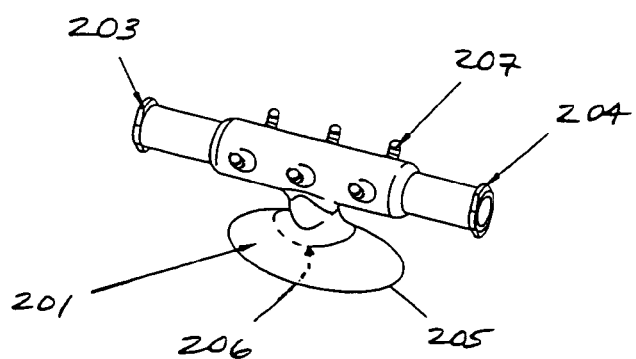
FIG. 12 is a perspective view of a top portion of the second embodiment shown in FIG. 11.

As shown in FIG. 12, the top portion 201 has a fitting 203 that is used to connect to a perfusion machine or other fluid source, for example, by tubing (not shown). The top portion 201, or a portion thereof, may be constructed of a clear or translucent material that allows a user to visually check for air bubbles. Any air that is present in the cannula 200 will collect at an upper portion of the top portion 201.

A second fitting 204 may be provided on the top portion 201 for priming and/or air bubble removal. The second fitting 204 comprises a port or valve for such purpose. The second fitting 204 may also be used to network multiple cannulas, for example, by connecting tubing either in series or parallel, as discussed above. Standard luer geometry or other structure may be used for fittings 203 and 204.

The top portion 201 has a top sealing surface 205. The top sealing surface 205 may be made of a soft elastomer, such as, for example, SANTOPRENE® made by advanced Elastomer Systems, silicone or flexible polyvinylchloride (PVC) and the like. The top sealing surface 205 in the embodiment shown in FIGS. 11-12 is a complex curved surface, for example, shaped like a football, being curved in both directions. Other suitable shapes, such as planar or cylindrical, are also contemplated. A cylindrically shaped surface may help to allow an aortic patch or other tissue to be fixed in its natural shape.

An opening 206 is provided in, preferably near the center of, the top sealing surface 205 to allow fluid flow. The opening 206 may be circular for example, for a single artery, or elliptical or oval, for example, to accommodate patches with multiple arteries, or may have other shapes. The top portion 201 preferably also has a plurality of protrusions or fingers 207 which may be used to secure the bottom portion 202, as described below.

Figure 13:
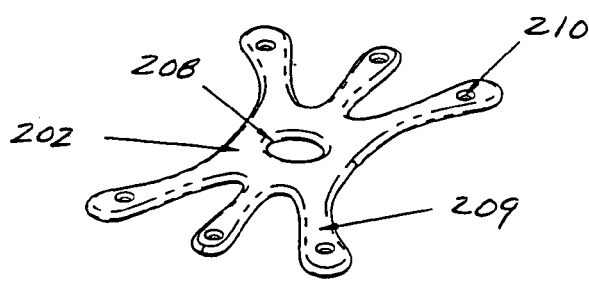
FIG. 13 is a perspective view of a bottom portion of the second embodiment shown in FIG. 11.

As shown in FIG. 13, the bottom portion 202 may comprise a preferably one-piece flexible part with a plurality of arms 209. One or more holes 210 or other fixing structure may be provided in the arms 209. The bottom portion 202 may preferably be made of a soft elastomer, such as, for example, SANTOPRENE® made by advanced Elastomer Systems, silicone or flexible polyvinylchloride (PVC) and the like.

Similar functionality may be accomplished with other arrangements, such as hinged clamps or suitable springs. The bottom portion 202 may comprise a rigid geometry that allows a snap fit either into or over the top portion 201. The bottom portion 202 may alternatively comprise a hinged part that closes to lock onto the top portion 201. A suitable spring may be designed to define a sealing surface and engage the top portion 201 to squeeze the aortic patch or other tissue to the top portion 201.

A hole 208 is located in, preferably in a central zone of, the bottom portion 202. The aortic patch or other tissue is positioned by feeding the patch or other tissue through the hole 208 and laying and/or spreading the patch or other tissue across the bottom portion 202. The hole 208 may be cut to a desired size and/or shape to accommodate different patch or other tissue sizes and/or patches or other tissues with multiple arteries. The artery(ies) is/are preferably aligned with the opening 206 in the top portion 201 and the arms 209 are stretched upward to bring the top and bottom portions 201 and 202 together and apply a force to compress the patch therebetween. The holes 210 in the arms 209 are engaged on the fingers 207 of the top portion 201 to close the cannula 200.

Multiple holes 210 may be provided on each of the arms 209 to allow the user to adjust tension, or other fastening structure may be used (e.g., hook and loop features, buckles, clamps, etc.).

Further, various configurations, shapes and/or sizes of the bottom portion 202 may be provided, for example, for differing anatomies. For example, for the configuration shown in FIG. 13, different numbers of arms, lengths of arms, and or sizes and/or shapes of opening may be provided.

Figure 14:
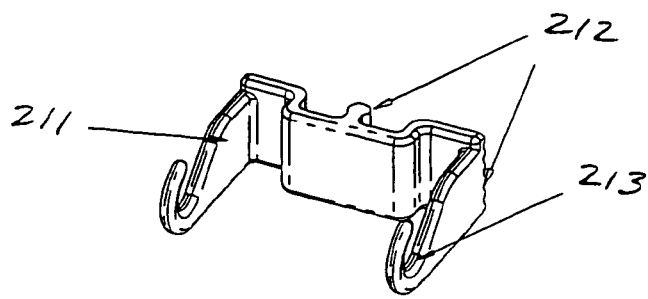
FIGS. 14 is a perspective view of the cannula mount of the second embodiment shown in FIG. 11.

As shown in FIG. 14, the positioning structure 211 may include locating features 212 that may be used to position the cannula 200 and the artery of the organ with respect to the organ and/or the organ platform or chair. The positioning structure 211 preferably provides a cradle 213 that receive the cannula 200 such that the cannula 200 may rotate about one axis. This allows the cannula 200 to hold the artery straight while preventing over-tensioning of the artery. As shown in this embodiment, the cradle 213 may be formed by hooks that engage the top portion 201 of the cannula 200.

Figure 15:
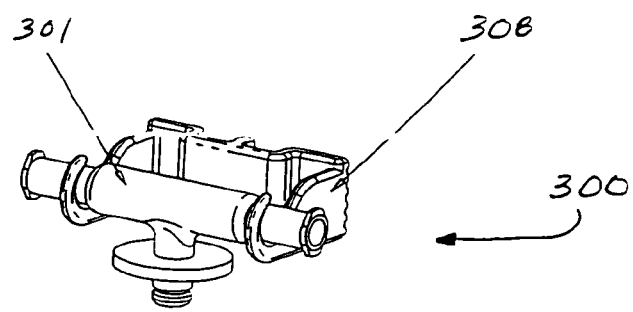
FIG. 15 is a perspective view of a third exemplary embodiment of a cannula and a cannula mount according to the invention.

FIG. 15 shows a perfusion clamping apparatus or cannula 300 according to a third exemplary embodiment of the invention. The cannula 300 is capable of connecting one or more arteries of an organ to a perfusion machine or system particularly when no aortic patch is available. This condition may arise due to difficult anatomy or living donors, when a portion of the aorta cannot be taken. Part of the cannula 300 is inserted directly into an artery and a suture, elastic band, vessel loops, adhesive, staple or other fastening mechanism is used to hold the artery in place.

The cannula 300 comprises a cannula body 301 and preferably also a cannula mount or positioning structure 308 that can be used to connect the cannula 300 to an organ platform or chair (not shown).

Figure 16:
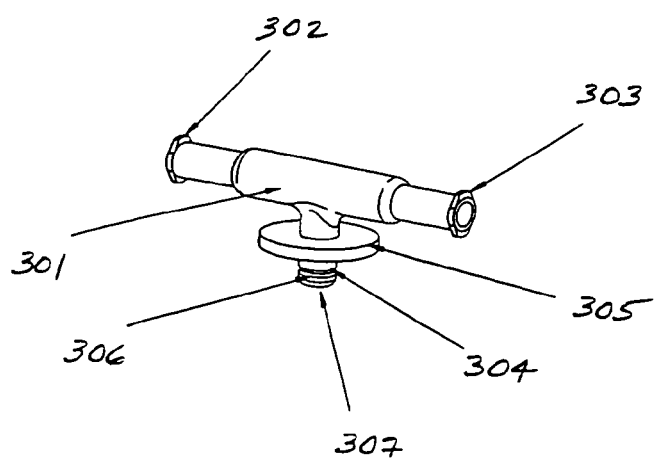
FIG. 16 is a perspective view of a cannula body of the third embodiment shown in FIG. 15.

As shown in FIG. 16, the cannula body 301 has a fitting 302 that is used to connect to a perfusion machine or other fluid source, for example, by tubing (not shown). The cannula body 301, or a portion thereof, may be constructed of a clear or translucent material that allows a user to visually check for air bubbles. Any air that is present in the cannula 300 will collect at an upper portion of the cannula body 301.

A second fitting 303 may be provided on the cannula body 301 for priming and/or air bubble removal. The second fitting 303 comprises a port or valve for such purpose. The second fitting 303 may also be used to network multiple cannulas, for example, by connecting tubing either in series or parallel, as described above. Standard luer geometry or other structure may be used for fittings 302 and 303.

The cannula body 301 also has a structure 304 that extends from the cannula body 301 and defines a lumen 307. Also, the cannula body 301 may have a flange 305 that facilitates insertion of the structure 304 and/or suturing of the artery.

The lumen 307 allows fluid flow through the structure 304. The structure 304 may be of various sizes to accommodate various anatomy and may have a securing feature 306 that cooperates with a fastening mechanism used to connect the artery to the cannula 300. The securing feature 306 may be a substantially annular groove, as shown in FIG. 16, a substantially annular ridge or series of ridges, or any other structure that is designed to cooperate with any known or hereafter developed fastening mechanism. The structure 304 may be made of a soft elastomer, such as, for example, SANTOPRENE® made by advanced Elastomer Systems, silicone or flexible polyvinylchloride (PVC) and the like.

Figure 17:
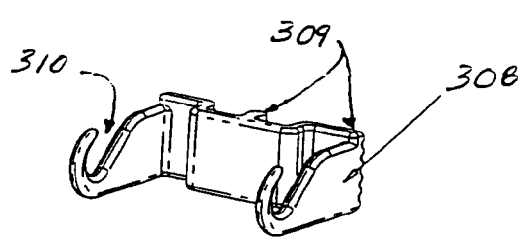
FIG. 17 is a perspective view of the cannula mount of the third embodiment shown in FIG. 15.

As shown in FIG. 17, the positioning structure 308 preferably has locating features 309 that may be used to position the cannula 300 and the artery of the organ, as described above. The positioning structure 308 provides a cradle 310 that preferably receives the cannula 300 such that the cannula 300 may rotate about one axis. This allows the cannula 300 to hold the artery straight while preventing over-tensioning of the artery. As shown in the embodiment of FIG. 17, the cradle 310 is formed by hooks that engage the cannula body 301.

Figure 18:
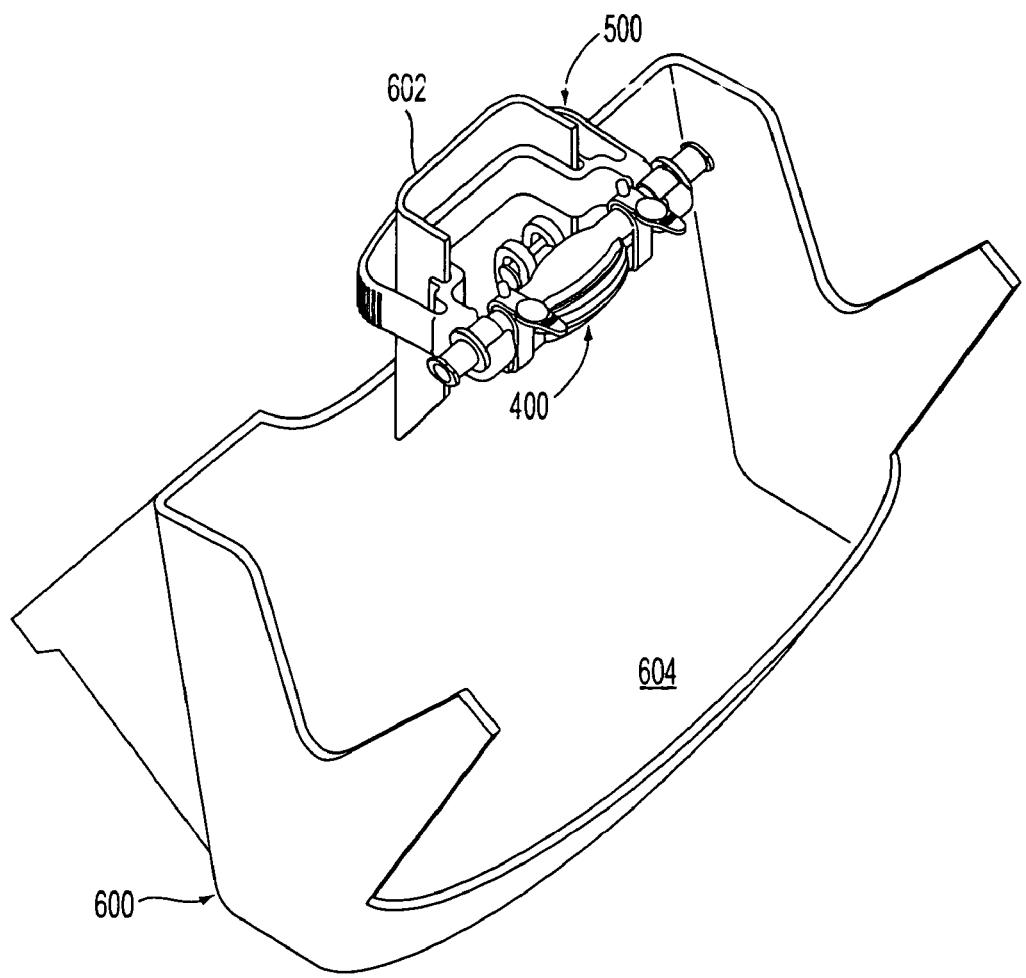
FIG. 18 is a perspective view of a fourth exemplary embodiment of a cannula, a cannula mount and a platform according to the invention.

FIG. 18 shows a perfusion clamping apparatus or cannula 400 according to a fourth exemplary embodiment of the invention assembled with a cannula mount 500 and a platform 600. The cannula 400 is capable of connecting one or more arteries of an organ to a perfusion machine or system (not shown), for example, by connection to tubing of the perfusion machine or system.

Figure 19:
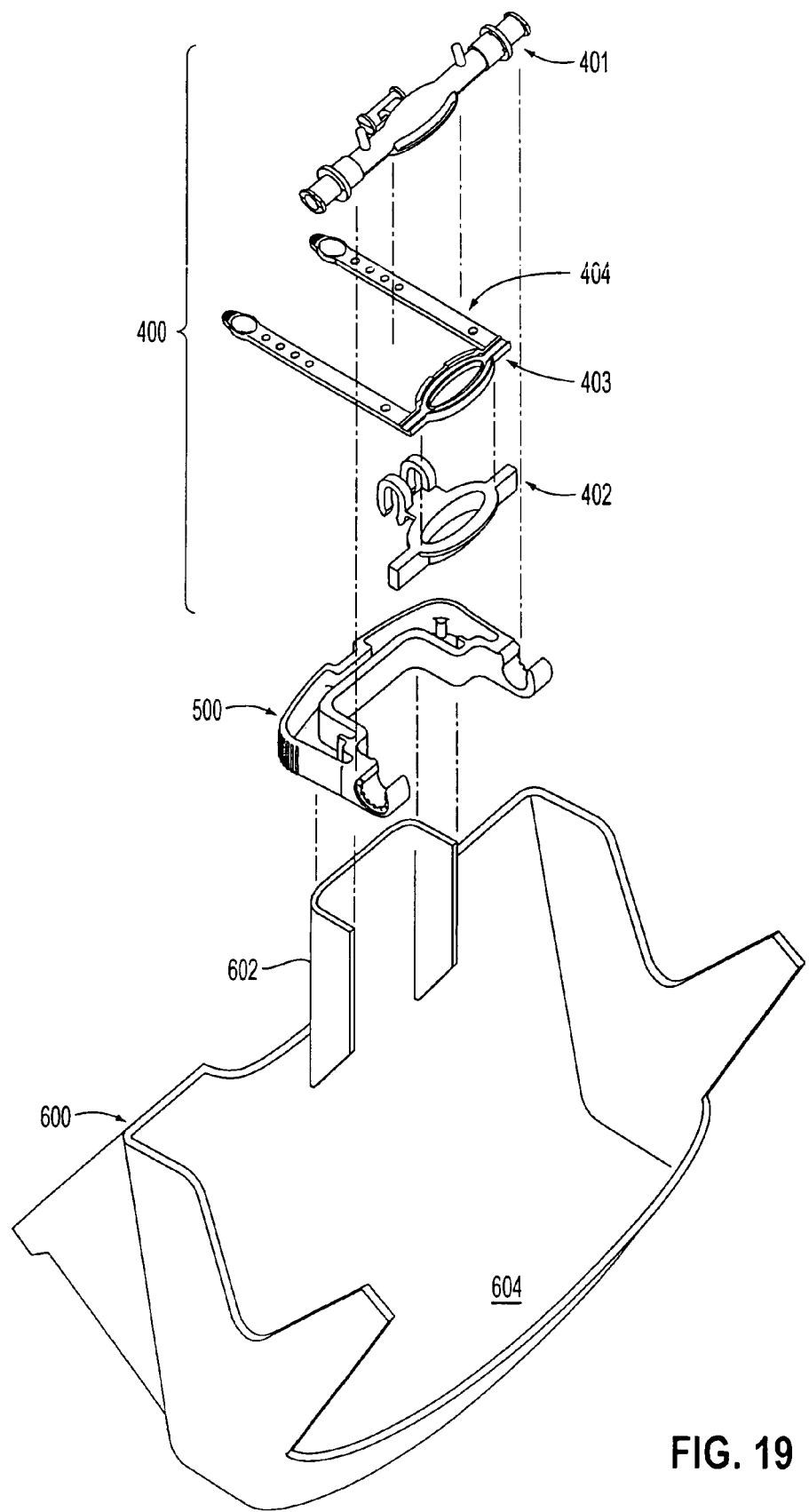
FIG. 19 is an exploded view of the fourth embodiment shown in FIG. 18.

The cannula 400 is shown in FIG. 18 in a closed or clamping condition and in FIG. 19 in an exploded condition. The cannula 400 comprises a top portion 401, a bottom portion 402, a sealing ring 403 and compression straps 404. As shown in FIG. 18, the cannula 400 is supported relative to the platform 600 via the cannula mount 500.

The top and bottom portions 401 and 402 seal to an aortic patch or other tissue by clamping the aortic patch or other tissue therebetween. The compression straps 404 may be used to force the top portion 401 and the bottom portion 402 together and may be made of a resilient material, such as an elastomer. The sealing ring 403 may be captured between the aortic patch or other tissue and the top portion 401 and/or the bottom portion 402. In the fourth embodiment, the sealing ring 403 is integral with the compression straps 404.

The top portion 401 has a first fitting 405 that is used to connect to a perfusion machine or other fluid source, for example, by tubing (not shown). The first fitting 405 is in fluid communication with the chamber formed when the top and bottom portions 401 and 402 are brought together. The top portion 401, or a portion thereof, may be constructed of a transparent or translucent material that allows a user to visually check for air bubbles. If the cannula 400 is oriented as shown, any air that is present in the cannula will collect at an upper portion 406 of the top portion 401.

A second fitting 407 may be provided on the top portion 401 for priming and/or air bubble removal. The second fitting 407 may comprise a port or valve for such purpose. The second fitting 407 is in fluid communication with at least one of the first fitting 405 and the chamber formed when the top and bottom portions 401 and 402 are brought together. The second fitting 407 may also be used to network multiple cannulas, for example, by connecting tubing in parallel, for example, by running a split infuse line to the first fitting of each cannula, or in series, for example, by connecting the first fitting of a cannula to the second fitting of another cannula. Standard luer geometry or other suitable structure may be used for fittings 405 and 407.

Figure 20:
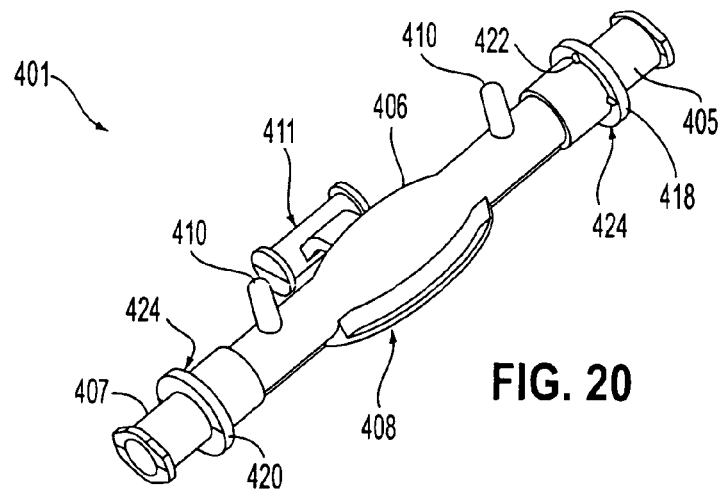
FIG. 20 is a perspective view of a top portion of the fourth embodiment shown in FIG. 18.

As shown in FIG. 20, the top portion 401 has a top sealing surface 408. The top sealing surface 408 may be made of a soft elastomer, such as, for example, SANTOPRENE® made by advanced Elastomer Systems. Any other suitable materials may be used as well, such as silicone or flexible polyvinylchloride (PVC) and the like. The top sealing surface 408 is shown in this embodiment as elliptical, although other suitable shapes, such as oval, circular and rectangular are also contemplated.

The top portion 401 may include fixing members 410 that hold a portion of the compression straps 404 with the cannula 400 in a clamping condition. The fixing members 410 are shown as posts in FIG. 20; however, any suitable structure that is capable of retaining the compression straps 404 may be used.

While the fixing members 410 are shown as part of the top portion 401, these members may be part of the bottom portion 402. In other words, such features of the cannula 400 may be reversed.

Figure 21:
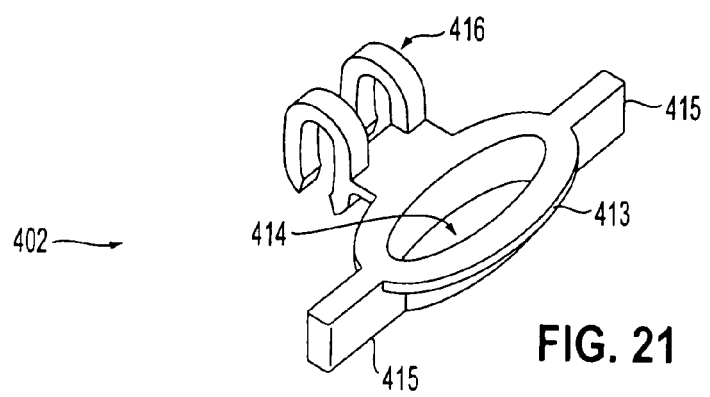
FIG. 21 is a perspective view of a bottom portion of the fourth embodiment shown in FIG. 18.

As shown in FIG. 21, the bottom portion 402 has a bottom sealing surface 412 that corresponds with the top sealing surface 408. The bottom sealing surface 412 may be made of a soft elastomer, as with the top sealing surface 408. The bottom sealing surface 412 may include a flange 413 that extends outwardly. The flange 413 may be used to position the aortic patch or other tissue prior to assembly, for example, by clamping the aortic patch or other tissue to the flange 413 with common surgical tools.

A hole 414 may be located in the bottom portion 402. The aortic patch or other tissue is positioned by feeding the patch through the hole 414 and laying and/or spreading the patch across the bottom sealing surface 412. The hole 414 may be designed to accept varying patch or other tissue sizes and/or patches or other tissues with multiple arteries.

The bottom portion 402 may include posts 415 that protrude outwardly. In use, the compression straps 404 can be wrapped around the posts 415. As discussed above, other suitable structures, either known or hereafter developed, that are capable of pressing and holding the top and bottom portions 401 and 402 together may be used in place of the compression straps 404.

The bottom portion 402 may include a complementary pre-positioning structure 416 that complements a pre-positioning structure 411 of the top portion 401. In the embodiment shown in FIGS. 18-19, the pre-positioning structure 411 is shown as a bar and the complementary pre-positioning structure 416 is shown as a pair of hooks. The hooks preferably engage the bar to allow the sealing surfaces 408 and 412 of the top and bottom portions 401 and 402 to remain parallel prior to closure and clamping, for example, by providing both pivoting and linear movement of the top and bottom portions 401 and 402 relative to one another. It should be understood that the structures 411 and 416 may be any suitable structures, either known or hereafter developed, that cooperate to provide pre-positioning of the top and bottom portions 401 and 402.

Figure 22:
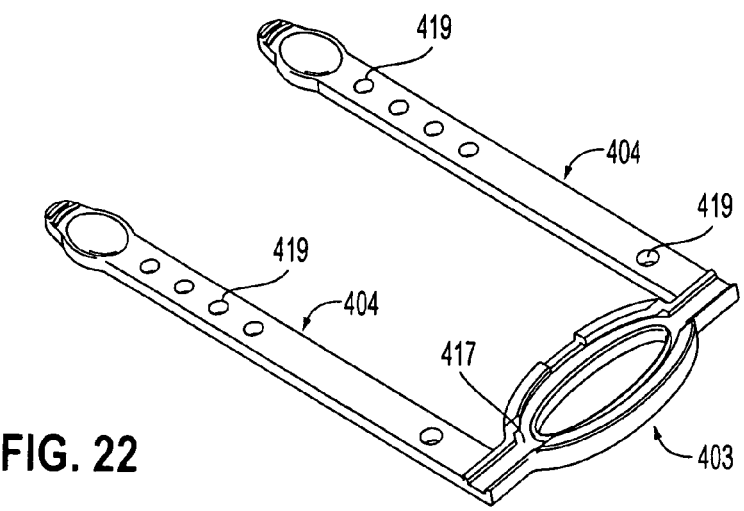
FIG. 22 is a perspective view of a sealing ring/compression straps of the fourth embodiment shown in FIG. 18.

An exemplary sealing ring 403 is shown in detail in FIG. 22. The sealing ring 403 may be shaped corresponding to the shape of the top and/or bottom portions 401 and 402, particularly the top and bottom sealing surfaces 408 and 412. The sealing ring 403 may be constructed of a soft material, such as SANTOPRENE® made by advanced Elastomer Systems, silicone or flexible polyvinylchloride (PVC) and the like, which allows the sealing ring 403 to surround and follow the contour of plaque or calcium deposits on the aortic patch or other tissue. The sealing ring 403 may have a shape that is complementary to the shape of at least one of the top sealing surface 408 and the bottom sealing surface 412. For example, as shown in FIG. 22, the sealing ring 403 may have a recess 417 that is shaped to snugly receive the top sealing surface 408.

Exemplary compression straps 404 are shown in detail in FIG. 22 as integral with the sealing ring 403. This arrangement eliminates a need to separately position the straps 404 relative to other parts of the cannula 400 as well as a need to secure a free end of each compression strap 104 to the top or bottom portions of the cannula 400. The tension of the compression straps 404 may be varied, for example, by engaging one of a plurality of holes 419 to fixing members 410 of the top portion 401. A textured surface, such as ridges, may be located at an end of each compression strap 404 to increase a user's grip for tensioning the compression straps 404. As the compression straps 404 are tensioned in use, the top and bottom portions 401 and 402 of the cannula 400 are pulled together to create a seal.

As discussed above, other suitable structures, either known or hereafter developed, that are capable of pressing and holding the top and bottom portions 401 and 402 together may be used in place of the compression straps 404. For example, rigid clips or compliant springs may be used in place of the compression straps 404.

As shown in FIG. 18, the cannula mount 500 is designed to position the cannula 400 relative to the organ (not shown) by supporting the cannula relative to the platform 600. The cannula mount 500 helps to hold the artery of an organ at a fixed tension and helps to keep the artery from being twisted or stressed by securely positioning the cannula 400 in relation to the platform 600.

Figure 23:
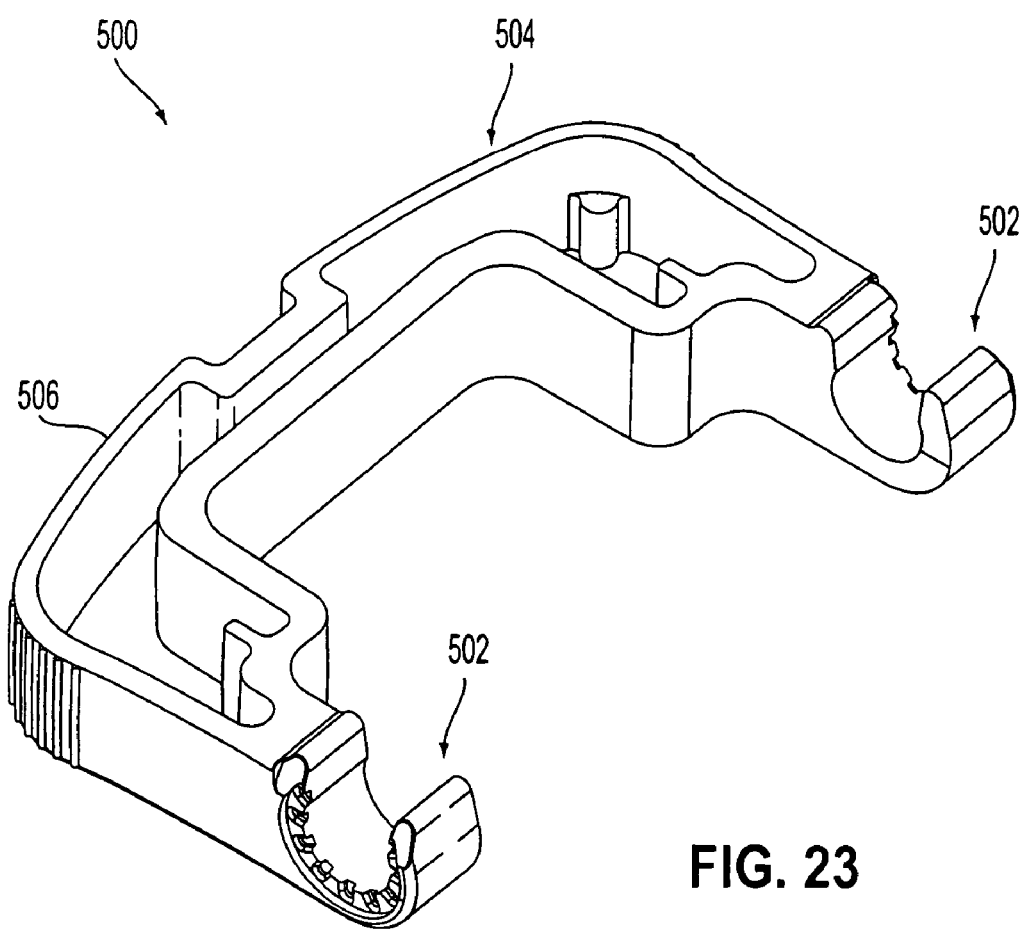
FIG. 23 of the cannula mount of the fourth embodiment shown in FIG. 18.

Details of the cannula mount 500 according to the fourth exemplary embodiment are shown in FIG. 23. It should be understood that certain features described as located on the cannula mount 500 or the cannula 400 may be reversed and located on the other. Further, certain features described as located on the cannula mount 500 or the platform 600 may be reversed and located on the other. Thus, the particular arrangement is illustrative and not limiting.

The cannula mount 500 has a pair of substantially "U" or "C" shaped portions 502 that are adapted to removably engage a connection arm, such as the first and second fittings 405 and 407, on the cannula 400. The cannula mount 500 has an attachment feature 504 adapted to engage a separate support structure, such as the platform 600. The separate support structure may be part of the platform 600 such that the cannula mount 500 is connected directly to the platform 600. Alternatively, the separate support structure may be independently connected to the platform 600 such that the cannula mount 500 is connected indirectly to the platform 600.

A feature of various exemplary embodiments of the cannula mount assembly according to this invention is that the cannula 400 may be positioned or located relative to the platform 600. For example, as described below, the cannula mount 500 may be movably positionable on the separate support structure. Alternatively, the separate support structure may be movably positionable on the platform 600. Thus, the height and/or position of the cannula 400 relative to the platform 600 may be adjusted to achieve a desired positional relationship between the cannula 400 and the platform 600 and/or an organ situated on the platform 600.

It should be understood that while the cannula 400 and the cannula mount 500 are shown as separate elements, the cannula mount 500 may be integral with part of the cannula 400.

The attachment feature 504 may be an open slot as shown in FIG. 23 that is designed to receive a mounting portion 602 that extends from a base 604 of the platform 600.

One side of the open slot 504 may be a resilient wall 506 that flexes to accommodate the mounting portion 602. Thus, when the mounting portion 602 is fitted through the open slot 504, the resilient wall 506 will press against the mounting portion 602 to hold the cannula mount 500 at a desired height above the base 604.

The cannula mount 500 may include a "release mechanism." For example, the resilient wall 506 may include a pair of substantially parallel extensions as shown in FIG. 23. In the exemplary embodiment, the resilient wall 506 will flex outward slightly when pressure is applied to a portion of the extensions, for example by applying a squeezing force to the extensions. The slight flexing of the resilient wall 506 may facilitate placement of the cannula mount 500 on the mounting portion 602 and may also facilitate movement of the cannula mount 500 on the mounting portion 602 to obtain a desired position of the cannula 400 relative to the platform 600. It should be understood that any other arrangement that allows a user to temporarily flex the resilient wall 506 may be used as well.

As shown in FIG. 20, the fittings 405 and 407 may include flange portions 418 and 420, respectively, that help a user to position the cannula 400 to locate the fittings 405 and 407 of the cannula 400 in the substantially "U" or "C" shaped portions 502, as shown in FIG. 18. The flange portions 418 and 420 each may have one or more protrusions 422 on an inner surface 424. The substantially "U" or "C" shaped portions 502 may have one or more complementary recesses 508 that are adapted to engage the protrusions 422 when the substantially "U" or "C" shaped portions 502 engage the fittings 405 and 407. The engagement of the recesses 508 and the protrusions 422 restrict rotation of the fittings 405 and 407 relative to the substantially "U" or "C" shaped portions 502. Thereby, rotation of the cannula 400 relative to the cannula mount 500 is restricted.

The configuration and/or features of the cannula mount 500 will vary depending on the configuration of the platform 600. For example, the open slot arrangement is illustrative, and any suitable connection between the cannula mount 500 and the platform 600 may be used.

The above described apparatus and methods may be used for small or child organs as well as for large or adult organs with modification as needed. Further, while the apparatus and methods are described above with respect to transplanting organs, the apparatus and methods can also be used to provide an artificial blood supply to other tissues and cell cultures, for example, artificial placenta cell cultures, for growing/cloning tissues and/or organ(s).

As an example, use of the cannulas 100, 200, 300 and 400 will be described in connection with harvesting an organ, such as a kidney. An organ recovery surgeon will first inspect the kidney geometry and select an appropriate cannula based on the kidney geometry. The blood flow to the kidney(s) is stopped and the kidney or kidneys are flushed of blood. The kidney or kidneys are removed from the donor, if possible, still attached to the aorta. If the kidney or kidneys cannot be removed with the aorta attached, the surgeon may select a cannula according to the third exemplary embodiment. Otherwise, the surgeon may select a cannula according to one of the other embodiments.

If both kidneys are removed with the aorta, they are split at the aorta after removal. One of the kidneys is placed onto the platform or chair. The renal artery with the attached aortic cuff is threaded through the hole in the bottom portion of the cannula. The aortic cuff is spread across the sealing surface of the bottom portion of the cannula. Then, the top portion of the cannula is aligned with the bottom portion and the top and bottom portions are brought together and secured, for example, by compression straps or by connecting part of the bottom portion to the top portion.

The cannula is then positioned and attached to the platform or chair so that a flow of fluid through the renal artery can be established, preferably with the renal artery extended straight.

Before or after the cannula is properly positioned, an infuse line is connected to the first fitting of the cannula. The second fitting is then opened and flow of a desired fluid is initiated. In embodiments, air bubbles can be detected visually through the cannula and vented via the second fitting. Once all air has been removed, the second fitting is closed, the cannula is inspected for leaks and the cannula is adjusted, if necessary. The kidney is then perfused.

When an aortic patch is not available, the renal artery may be cut and the cannula inserted into the renal artery. Then, the renal artery is fastened to the cannula using an appropriate fastening mechanism, such as a suture. The cannula may be positioned and attached to the platform or chair and purged as described above.

The platform or chair may be placed or located in an organ cassette as discussed above, which is placed in a transport system that cools the organ cassette and the organ on the platform. The cannula may be connected to tubing of a perfusion system of the transport system and, if needed, purged after connection to the perfusion system.

The organ cassette allows an organ to be easily and safely moved between apparatus for perfusion, storing, analyzing and/or transporting the organ. The organ cassette may be configured to provide uninterrupted sterile conditions and efficient heat transfer during transport, recovery, analysis and storage, including transition between the transporter, the profusion apparatus and the organ diagnostic apparatus. The organ transporter allows for transportation of an organ over long distances. The organ transporter may be used for various organs, such as the kidneys, and may be adapted to more complex organs such as the liver, having multiple vascular structures, for example the hepatic and portal vasculatures of the liver. The organ transporter includes features of an organ perfusion apparatus, such as sensors and temperature controllers, as well as cassette interface features. The perfusion apparatus, transporter, cassette and organ diagnostic apparatus may be networked to permit remote management, tracking and monitoring of the location and therapeutic and diagnostic parameters of the organ or organs being stored or transported. The information systems may be used to compile historical data of organ transport and storage, and provide cross-referencing with hospital and United Network for Organ Sharing (UNOS) data on the donor and recipient. The systems may also provide outcome data to allow for ready research or profusion parameters and transplant outcomes. Various exemplary embodiments of the cannulas and the cannula mount assemblies according to this invention facilitate interconnection between an organ and the perfusion apparatus, transporter, cassette and organ diagnostic apparatus.

While the invention has been described in conjunction with specific embodiments thereof, it is evident that many alternatives, modifications and variations may be apparent to those skilled in the art. Accordingly, the exemplary embodiments of the invention as set forth herein are intended to be illustrative, not limiting. Various changes may be made without departing from the spirit and scope of the invention.

What is claimed is:

1. A cannula for connecting an organ to an external fluid flow system, the cannula comprising:
a first portion;
a second portion,
a pre-positioning structure formed on the first portion;
a complementary pre-positioning structure formed on the second portion. the pre-positioning structure and the complementary pre-positioning structure arranged to engage each other while permitting relative movement of the first and second portions, wherein:
a chamber is formed when the first and second portions are brought together;
a first fitting is disposed on one of the first and the second portions, the first fitting being in fluid communication with the chamber;
the second portion has a hole, the hole being in fluid communication with the chamber and being adapted to receive a section of tissue of the organ;

at least one sealing surface is adapted to secure the section of tissue by pressure applied to the section of secured tissue between the first and second portions when the first and second portions are brought together;

at least one of the first fitting and the hole is adapted to allow fluid flow from the external fluid flow system into the section of tissue, and the relative movement permitted by the engagement of the pre-positioning structure and the complementary pre-positioning structure allows the first portion and the second portion to be positioned relative to each other such that a first sealing surface on the first portion is parallel to a second sealing surface on the second portion when the first sealing surface and the second sealing surface are spaced apart and allows the first and second portions to be brought together, while maintaining the first sealing surface parallel to the second sealing surface, to secure the section of tissue.

2. The cannula of claim 1, wherein the first fitting and the hole are configured such that fluid flow through the first fitting is substantially perpendicular to fluid flow through the hole.

3. The cannula of claim 1, wherein at least a portion of at least one of the first and second portions that forms part of the chamber is one of a transparent material and a translucent material.

4. The cannula of claim 1, further comprising:
at least one fixing member on one of the first and second portions; and
at least one compression strap arranged to wrap around at least part of the first portion and at least part of the second portion and to engage the fixing member so that the first and second portions are brought together.

5. The cannula of claim 4, further comprising a sealing ring disposed between the first and second portions, the compression strap extending from the sealing ring.

6. The cannula of claim 5, the sealing ring being integral with the compression strap.

7. The cannula of claim 4, further comprising:
at least one engagement member on one of the first and second portions; and
a complementary engagement member at a free end of the compression strap;
wherein the engagement member is arranged to engage the complementary engagement member while the compression strap is wrapped around at least part of the first portion and at least part of the second portion and engages the fixing member so that the first and second portions are brought together.

8. The cannula of claim 1 wherein the relative movement permitted by the engagement of the pre-positioning structure and the complementary pre-positioning structure comprises a pivoting movement that allows the first portion and the second portion to be positioned relative to each other such that the first sealing surface is parallel to the second sealing surface.

9. The cannula of claim 1, wherein the relative movement permitted by the engagement of the pre-positioning structure and the complementary pre-positioning structure comprises a linear movement that allows the first and second portions to be brought together, while maintaining the first sealing surface parallel to the second sealing surface.

10. The cannula of claim 1, wherein the relative movement permitted by the engagement of the pre-positioning structure and the complementary pre-positioning structure comprises a pivoting movement that allows the first portion and the second portion to be positioned relative to each other such that the first sealing surface is parallel to the second sealing surface and a linear movement that allows the first and second portions to be brought together, while maintaining the first sealing surface parallel to the second sealing surface.

11. The cannula of claim 1, wherein a flange extends from an outer surface of the second portion.

12. The cannula of claim 1, further comprising:
at least one sealing ring disposed between the top and bottom portions.

13. The cannula of claim 12, wherein the sealing ring comprises an elastomeric material.

14. The cannula of claim 12, wherein the first portion has a first sealing surface, the second portion has a second sealing surface, and the sealing ring has a shape complementary to a shape of at least one of the first and second sealing surfaces.

15. The cannula of claim 14, wherein at least one of the first and second sealing surfaces comprises at least one of ribs, ridges, cuts and protrusions and the sealing ring comprises a plurality of complementary details corresponding to the at least one of ribs, ridges, cuts and protrusions.

16. The cannula of claim 1, wherein the first portion has a first sealing surface, the second portion has a second sealing surface, and at least one of the first and second sealing surfaces comprises an elastomeric material.

17. The cannula of claim 16, wherein at least one of the first and second sealing surfaces comprises at least one of ribs, ridges, cuts and protrusions.

18. The cannula of claim 1, the at least one sealing surface and one of the first and second portions being disposed on opposite sides of the section of secured tissue.

19. The cannula of claim 18, the at least one sealing surface being unitary with only the other of the first and second portions.

20. The cannula of claim 1, the at least one sealing surface being planar and disposed such that the section of secured tissue contacts and extends along the planar surface.

21. The cannula of claim 1, an upper portion of the first portion opposite of the hole is designed to collect gas separate from a fluid flow through the first fitting, the chamber and the hole.

22. A cannula for connecting an organ to an external fluid flow system, the cannula comprising:
a first portion; and
a second portion, wherein:
a chamber is formed when the first and second portions are brought together;
a first fitting is disposed on one of the first and the second portions, the first fitting being in fluid communication with the chamber,
the second portion has a hole, the hole being in fluid communication with the chamber and being adapted to receive a section of tissue of the organ;
at least one sealing surface is adapted to secure the section of tissue by pressure applied to the section of secured tissue between the first and second portions when the first and second portions are brought together; and
at least one of the first fitting and the hole is adapted to allow fluid flow from the external fluid flow system into the section of tissue,
wherein the chamber is designed to collect and trap gas separate from a fluid flow through the first fitting, the chamber and the hole.

23. The cannula of claim 1, further comprising a second fitting formed on one of the first and second portions, the second fitting being in fluid communication with the chamber that is formed when the first and second portions are brought together.

24. The cannula of claim 23, wherein the first fitting and the hole are configured such that fluid flow through the second fitting is substantially perpendicular to fluid flow through the hole.

25. The cannula of claim 23, wherein the second fitting comprises at least one of a vent and a valve.

26. The cannula of claim 23, wherein the second fitting is adapted to connect to a first fitting of a second cannula.

27. A method for connecting an organ to a fluid flow system, comprising:
providing the cannula of claim 1; and
securing a section of tissue of an organ between the first and second portions of the cannula.

28. The method of claim 27, further comprising:
connecting the first fitting to a fluid flow system; and
visually checking for gas in the cannula after connecting the first fitting to a fluid flow system.

29. The method of claim 27, further comprising:
connecting the first fitting to a fluid flow system; and
opening a second fitting, in communication with the chamber formed when the first and second portions are brought together, to allow gas in the cannula to be removed from a flow of liquid between the fluid flow system and the organ.

30. The method of claim 27, further comprising:
connecting the first fitting to a fluid flow system; and
connecting a second fitting of the cannula to a first fitting of another cannula to allow a flow of liquid between the fluid flow system and both cannulas.

31. The method of claim 27, further comprising:
providing a cannula mount adapted to engage and support the cannula; and
engaging the cannula with the cannula mount after securing the section of tissue.

32. The method according to claim 31, further comprising adjusting a position of the cannula relative to the cannula mount after engaging the cannula with the cannula mount.

33. The method of claim 32, wherein adjusting the position of the cannula comprises rotating the cannula relative to the cannula mount.

34. The method according to claim 31, further comprising:
providing a platform adapted to support the organ and to engage and support the cannula mount;
engaging the cannula mount with the platform after securing the section of tissue; and
placing the organ on the platform.

35. The method of claim 34, further comprising adjusting a position of the cannula mount relative to the platform after engaging the cannula mount with the platform.

36. The method of claim 35, wherein adjusting the position of the cannula mount comprises adjusting a distance of the cannula relative to a portion of the platform that supports the organ.

37. A method for connecting an organ to a fluid flow system, comprising:
providing the cannula of claim 17; and
securing a section of tissue of an organ between the first and second portions of the cannula.

38. The method of claim 37, further comprising:
connecting the first fitting to a fluid flow system; and
visually checking for gas in the cannula after connecting the first fitting to a fluid flow system.

39. The method of claim 37, further comprising:
connecting the first fitting to a fluid flow system; and
opening a second fitting on the first portion to allow gas in the cannula to be removed from a flow of liquid between the fluid flow system and the organ.

40. The method of claim 37, further comprising:
connecting the first fitting to a fluid flow system; and
connecting a second fitting of the cannula to a first fitting of another cannula to allow a flow of liquid between the fluid flow system and both cannulas.

41. The method of claim 37, further comprising:
providing a cannula mount adapted to engage and support the cannula; and
engaging the cannula with the cannula mount after securing the section of tissue.

42. The method according to claim 41, further comprising adjusting a position of the cannula relative to the cannula mount after engaging the cannula with the cannula mount.

43. The method of claim 42, wherein adjusting the position of the cannula comprises rotating the cannula relative to the cannula mount.

44. The method according to claim 41, further comprising:
providing a platform adapted to support the organ and to engage and support the cannula mount;
engaging the cannula mount with the platform after securing the section of tissue; and
placing the organ on the platform.

45. The method of claim 44, further comprising adjusting a position of the cannula mount relative to the platform after engaging the cannula mount with the platform.

46. The method of claim 45, wherein adjusting the position of the cannula mount comprises adjusting a distance of the cannula relative to a portion of the platform that supports the organ.

47. A cannula for connecting an organ to an external fluid flow system, the cannula comprising:
a first portion;
a second portion; and
a connection between the first portion and the second portion, wherein:
a chamber is formed when the first and second portions are brought together;
a first fitting is disposed on one of the first and the second portions, the first fitting being in fluid communication with the chamber;
the second portion has a hole, the hole being in fluid communication with the chamber and being adapted to receive a section of tissue of the organ;
at least one sealing surface is adapted to secure the section of tissue by pressure applied to the section of secured tissue between the first and second portions when the first and second portions are brought together;
at least one of the first fitting and the hole is adapted to allow fluid flow from the external fluid flow system into the section of tissue; and the connection allows both relative linear motion and relative rotational motion between the first portion and the second portion.

48. A cannula for connecting an organ to an external fluid flow system, the cannula comprising:
- a first portion;
- a second portion, and
- a connection between the first portion and the second portion, wherein:
- a chamber is formed when the first and second portions are brought together;
- a first fitting is disposed on one of the first and the second portions, the first fitting being in fluid communication with the chamber;
- the second portion has a hole, the hole being in fluid communication with the chamber and being adapted to receive a section of tissue of the organ;
- at least one sealing surface is adapted to secure the section of tissue by pressure applied to the section of secured tissue between the first and second portions when the first and second portions are brought together;
- at least one of the first fitting and the hole is adapted to allow fluid flow from the external fluid flow system into the section of tissue; and
- the connection allows relative linear motion between the first portion and the second portion.

* * * * *

UNITED STATES PATENT AND TRADEMARK OFFICE
CERTIFICATE OF CORRECTION

| | | |
|---|---|---|
| PATENT NO. | : 8,361,091 B2 | Page 1 of 1 |
| APPLICATION NO. | : 10/646801 | |
| DATED | : January 29, 2013 | |
| INVENTOR(S) | : Schein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2172 days.

Signed and Sealed this
Eighteenth Day of November, 2014

Michelle K. Lee
*Deputy Director of the United States Patent and Trademark Office*